(12) United States Patent
Schabbach et al.

(10) Patent No.: US 8,915,881 B2
(45) Date of Patent: Dec. 23, 2014

(54) INJECTION DEVICE WITH HOLDING MEANS TO PREVENT UNINTENTIONAL MOVEMENTS OF PISTON ROD

(75) Inventors: Michael Schabbach, Frankfurt (DE); Axel Roth, Frankfurt (DE); Gerhard Hambrecht, Rosenberg (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 774 days.

(21) Appl. No.: 13/126,321

(22) PCT Filed: Dec. 1, 2009

(86) PCT No.: PCT/EP2009/066094
§ 371 (c)(1),
(2), (4) Date: Dec. 30, 2011

(87) PCT Pub. No.: WO2010/063687
PCT Pub. Date: Jun. 10, 2010

(65) Prior Publication Data
US 2012/0095412 A1 Apr. 19, 2012

(30) Foreign Application Priority Data

Dec. 4, 2008 (EP) ..................................... 08021046

(51) Int. Cl.
*A61M 37/00* (2006.01)
*A61M 5/315* (2006.01)
*A61M 5/24* (2006.01)

(52) U.S. Cl.
CPC ... *A61M 5/31551* (2013.01); *A61M 2005/3151* (2013.01); *A61M 5/31535* (2013.01);
(Continued)

(58) Field of Classification Search
USPC ........................ 604/131, 151, 154, 155, 228
See application file for complete search history.

(56) References Cited

U.S. PATENT DOCUMENTS

| 4,498,904 | A | 2/1985 | Turner et al. |
| 6,800,071 | B1 * | 10/2004 | McConnell et al. ........ 604/155 |
| 2008/0119796 | A1 | 5/2008 | Graf et al. |

FOREIGN PATENT DOCUMENTS

| DE | 331 326 C | 1/1921 |
| DE | 299 07 881 U1 | 9/2000 |

(Continued)

OTHER PUBLICATIONS

International Search Report for corresponding International App. No. PCT/EP2009/066094, mailed Feb. 23, 2010.
European Search Report for corresponding European App. No. 08021046, dated Sep. 8, 2009.

* cited by examiner

*Primary Examiner* — Scott Medway
(74) *Attorney, Agent, or Firm* — McDonnell Boehnen Hulbert & Berghoff LLP

(57) ABSTRACT

The invention relates to a injection device, comprising a housing being adapted to receive in its proximal housing portion a container with an injection fluid and to receive in its distal housing portion a dose setting and injection mechanism, wherein the mechanism includes a piston rod being axially displaceable with respect to the housing for dispensing injection fluid from the container, wherein the piston rod has an outer thread and is arranged torque proof with respect to the housing, dose setting means comprising a threaded element, which threaded element has an inner thread being in engagement with the outer thread of the piston rod, is designed so that its axial position relative to the housing is changeable and is rotatable relative to the piston rod and relative to the housing during setting of an injection dose, wherein the dose setting means are designed such that the threaded element is held in torque proof manner relative to the piston rod and to the housing during the injection of the beforehand set injection dose in such a manner that the threaded element and the piston rod are axially displaceable together with respect to the housing, wherein the mechanism further comprises holding means being in contact with the piston rod and being designed such that the axial displacement of the piston rod can be substantially immobilized during use of the device except for the dispensing of the injection dose. It is proposed according to the invention that the holding means are axially fixed with respect to the housing.

12 Claims, 3 Drawing Sheets

(52) U.S. Cl.
CPC .... *A61M 5/31558* (2013.01); *A61M 2005/2407* (2013.01); *A61M 2205/583* (2013.01); *A61M 5/31585* (2013.01); *A61M 2005/3152* (2013.01); *A61M 5/24* (2013.01); *A61M 5/31505* (2013.01); *A61M 2005/2488* (2013.01)
USPC .......... 604/155; 604/131; 604/151; 604/154; 604/228

(56) References Cited

FOREIGN PATENT DOCUMENTS

| | | |
|---|---|---|
| EP | 0496141 A | 7/1992 |
| EP | 0594349 | 4/1994 |
| EP | 1610848 B1 | 10/2006 |
| GB | 789027 A | 1/1958 |

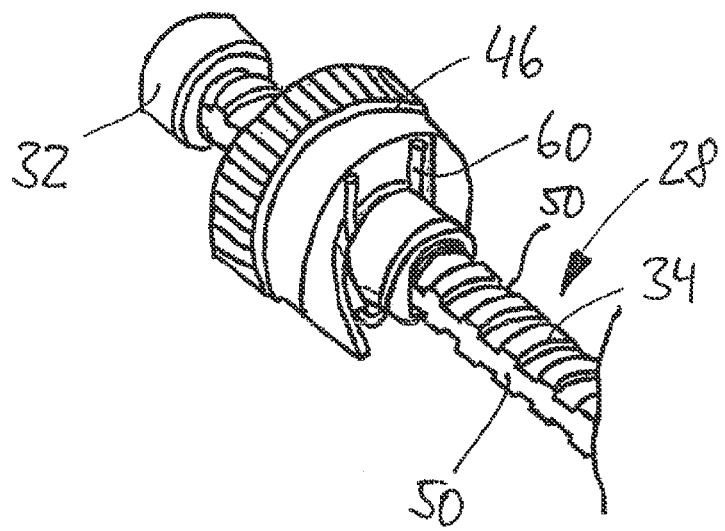
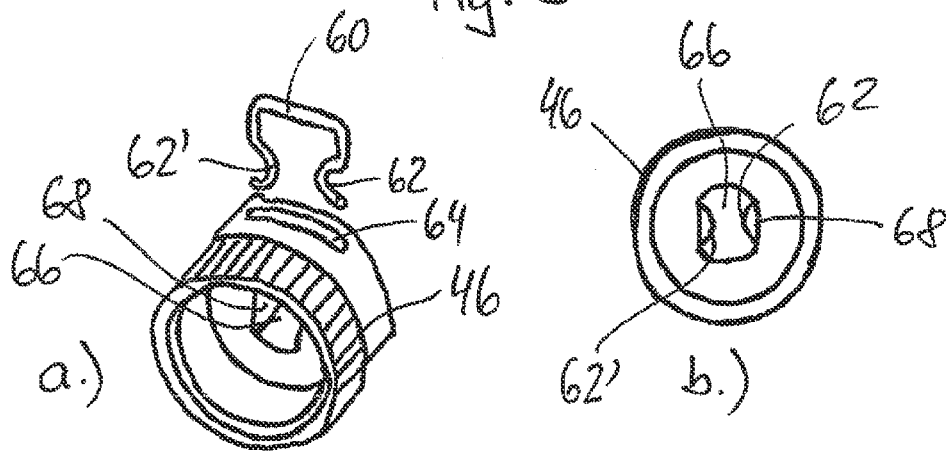
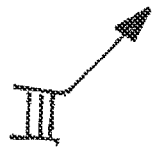
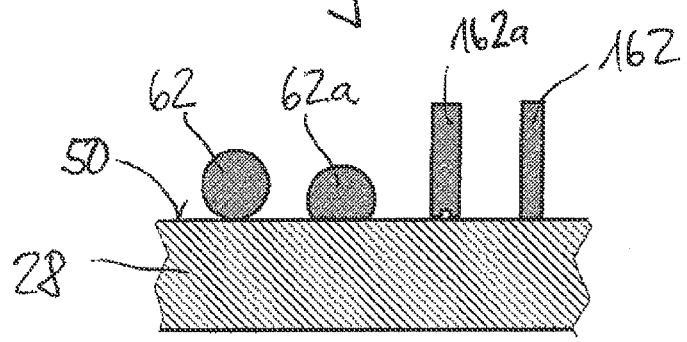

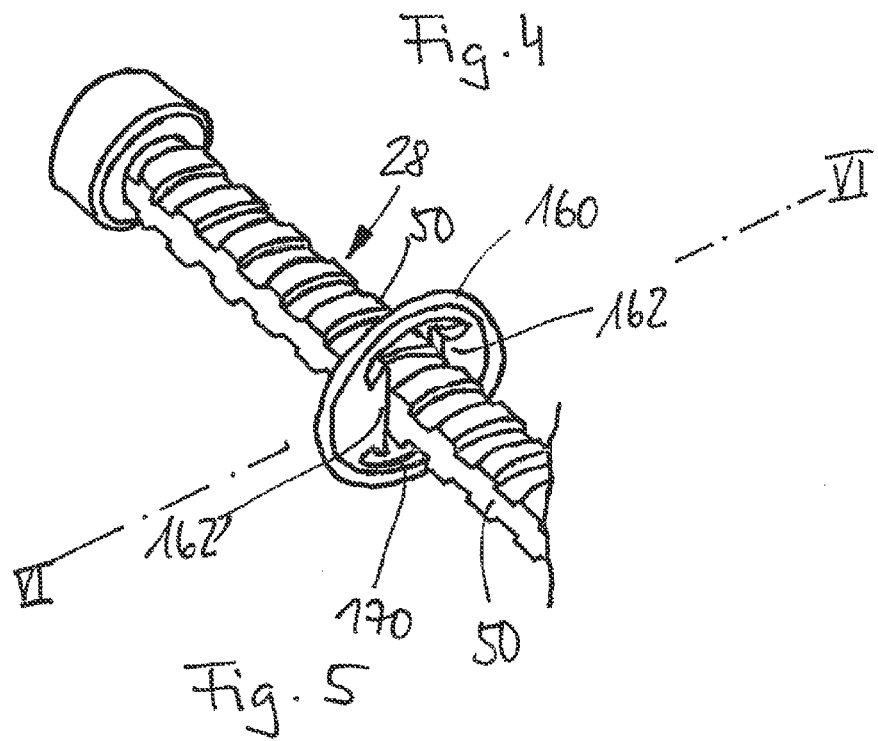
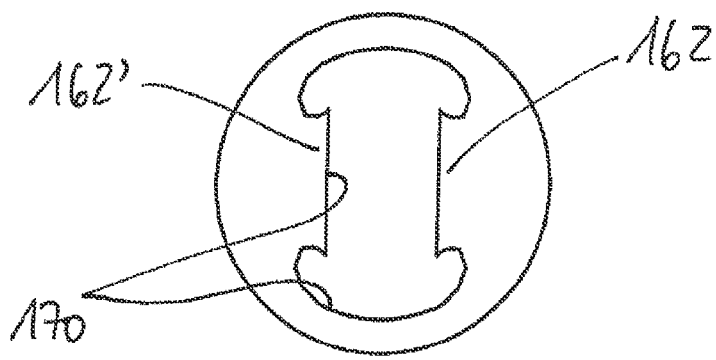
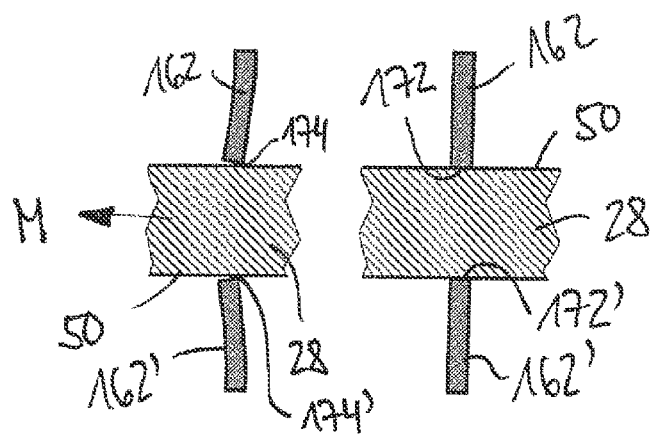

INJECTION DEVICE WITH HOLDING MEANS TO PREVENT UNINTENTIONAL MOVEMENTS OF PISTON ROD

CROSS REFERENCE TO RELATED APPLICATIONS

The present application is a U.S. National Phase Application pursuant to 35 U.S.C. §371 of International Application No. PCT/EP2009/066094 filed Dec. 1, 2009, which claims priority to Patent Application No. EP 08021046.1 filed on Dec. 4, 2008. The entire disclosure contents of these applications are herewith incorporated by reference into the present application.

TECHNICAL FIELD

This invention relates to an injection device, comprising a housing being adapted to receive in its proximal housing portion a container with an injection fluid and to receive in its distal housing portion a dose setting and injection mechanism, wherein the mechanism includes a piston rod being axially displaceable with respect to the housing for dispensing injection fluid from the container, wherein the piston rod has an outer thread and is arranged torque proof with respect to the housing, dose setting means comprising a threaded element, which threaded element has an inner thread being in engagement with the outer thread of the piston rod, is designed so that its axial position relative to the housing is changeable and is rotatably relative to the piston rod and relative to the housing during setting of an injection dose, wherein the dose setting means are designed such that the threaded element is held in torque proof manner relative to the piston rod and to the housing during the injection of the beforehand set injection dose in such a manner that the threaded element and the piston rod are axially displaceable together with respect to the housing, wherein the mechanism further comprises holding means being in contact with the piston rod and being designed such that the axial displacement of the piston rod can be immobilized or substantially immobilized during use of the device except for the dispensing of the injection dose.

BACKGROUND

Such an injection device is known from document DE 299 07 881 U1, which discloses an injector device for automatically, in a first step injecting, the needle, and in a second step dispensing an injection dose, the injection dose being beforehand set by manual operation. In this device the injection operation is mainly effected by a pre-stressed spring which urges the injection mechanism toward a proximal end (side of a patient) of the device, when the dispensing of an injection dose is activated. In the first step (needle injection) the aforementioned spring acts on a threaded sleeve having an inner thread being in contact with the outer thread of the piston rod. The piston rod is coupled by a slipping clutch (holding means) with further sleeves that are fixedly connected with the container having the needle at its proximate end. In the first step, the spring urges via threaded element, piston rod, slipping clutch, and sleeves in axial direction on the container so that the needle is moved together with the container to a stop position. When this stop position is reached, the pre-stressed spring urges further on the threaded element and the piston rod in proximal direction, so that the slipping clutch having ratchet teeth on the piston rod and a corresponding ratchet arm on a further sleeve, is disengaged. This enables the piston rod to be axially displaced in order to press on the piston within the container and to dispense the beforehand set injection dose. The slipping clutch, namely the ratchet arm, is arranged on these sleeves being in contact with the container, so that the whole slipping clutch is axially moveable with respect to the housing of the injection device.

Furthermore, there is known a similar injection device from document EP 1 610 848 B1 having no needle expelling function and no holding means.

It is often to observe that a little bit of the medicament to be injected leaks from the needle when a patient is rotating a dose knob of the dose setting mechanism. Typically, there appears firstly a droplet on the needle point. When further rotating action is made on the dose knob this droplet grows further and in extreme examples the medicament drop falls down. Such phenomena are unintentional and are making the patient insecure, although these phenomena are not safety relevant in addition to the contamination of the environment. Such phenomena are due to manufacturing tolerances, material surface properties, undesirable inner frictions and plays within the injection mechanism, which leads to unwanted axial movements of the piston rod dispensing medicament from the cartridge.

Such phenomena could be avoided by extremely precise manufacturing and frictionless construction of the different components of the injection mechanism. This is very costly and it is very difficult to achieve such precise manufacturing, also bearing in mind, that the components are rather small.

SUMMARY

It is therefore the object of the present invention to provide an injection device, wherein unwanted droplet formation is avoided.

This problem is solved by a generic injection device, wherein the holding means are axially fixed with respect to the housing.

When the holding means being in contact with the piston rod but axially fixed with respect to the housing and being designed such that the axial displacement of the piston rod can be substantially immobilized during use of the device except for the dispensing of other injection dose, the holding means are not subjected to any play of the injection mechanism, as in contrast to the slipping clutch of DE 299 07 871 A1 having parts axially displaceable with respect to the housing. When the holding means are arranged fixedly relative to the housing of the injection device, an unwanted axial displacement of the piston rod can effectively avoided as forces due to plays of the mechanism or due to inner friction can be received by the housing by means of the holding means. Therefore, there is no need for further improvement of the precision of manufacturing, so that the holding means axially fixed with respect to the housing provide a cost-saving possibility to avoid the formation of droplets during normal use of the injection device.

Preferably, the holding means at least partially encompass the piston rod. Such an encompassing allows a good transfer of forces acting axially on the piston rod to the housing, so that the piston rod can be held immobilized.

Preferably, the piston rod has two planar longitudinal outer surfaces cut in the outer thread and being arranged in parallel to each other on opposing sides of the piston rod, wherein the holding means are expediently in contact with both parallel outer surfaces of the piston rod and exert a compressive force on the piston rod. In this respect it is preferred that the holding means act as a clamp having two clamp portions each of which being in contact with a respective planar outer surface of the piston rod. Furthermore, it is proposed that the clamping portions are designed in such a manner, that they exert static friction on the piston rod being as high as to prevent unintentional axial displacement of the piston rod. Furthermore, the two clamping portions are preferably designed in such a manner, that they exert kinetic friction on the piston rod being as small as not to or only slightly interfere with the required axial displacement of the piston rod during dispensing an injection dose.

The acting of a holding means preferably by clamping portions from two sides on the parallel and opposing outer surfaces of the piston rod leads to the advantage that the exerted compressive force only acts on the piston rod. The holding means do not act upon the piston rod unilaterally so that the compressive force would have to be supported especially in radial direction by parts of the injection mechanism. In fact, the compressive forces produced by each of the two clamping portions pressing on opposing sides of the piston rod neutralize each other, so that no additional forces are generated, which have to be supported by the injection mechanism. The two clamping portions are automatically centering the holding means with respect to the piston rod. The holding means having two clamping portions lead to a frictionally engaging connection with the piston rod, wherein the static friction should be as high as to transfer forces due to plays in the injection mechanism securely to the housing. Furthermore, the frictionally engaged connection should allow for an easy dispensing of an injection dose, i.e. a smoothly axial displacement of the piston rod with respect to the holding means, when the injection dose is manually dispensed by pressing on a distal end of the injection device.

According to an embodiment, the holding means, preferably only the clamping portions, are deformable, preferably elastically deformable and/or deflectable, wherein it is further proposed that the clamping portions are deformable between a holding state and a sliding state, wherein a contact area between the clamping portion and the planar outer surfaces of the piston rod is maximal in the holding state. Such an arrangement leads to the advantage that the static friction being naturally higher than the kinetic friction, can be further increased with respect to the kinetic friction of the holding means, as a maximal contact area in the holding state leads to a maximum possible static friction. When the clamping portions are elastically deformed during axial displacement of the piston rod, the end faces of the clamping portions are slightly tilted with respect to the outer surfaces of the piston rod, so that a smaller contact area with the piston rod is achieved. This allows for an easy axial displacement of the piston rod as the kinetic friction is lowered with respect to a case in which a contact area remains maximal during such axial movement of the piston rod.

Preferably the holding means are made from plastics, preferable of one of a plastics or a blend of the group of polyethylene, polypropylene, polyamide, polytetrafluoroethylene, polyoxymethylene, polyurethane.

The holding means have preferably the form of a disc with an opening having an inner contour defining the clamping portions. Such a disc is most preferably made from plastics and can be manufactured in an easy way for example as molding part or similar.

In an alternative embodiment the holding means are preferably made from metal, especially from spring steel, wherein the holding means are preferably made from a bent wire. When the holding means have the form of a bent wire, the clamping portions can have a curvature being convex in a direction to the piston rod.

In both alternatives, namely holding means in form of a plastic disc and in form of a bent metal wire, the clamping portions are formed in such a way, that the required frictional forces are evoked, so that unintentional axial displacement of the piston rod can be avoided.

The holding means have preferably a symmetrical form with respect to the plane containing the longitudinal axis of the piston rod and being in parallel to the planar outer surfaces of the piston rod.

Furthermore, the holding means can be arranged at a proximal end of the distal housing portion close to a connection portion where the proximal housing portion and the distal housing portion are removable attached to each other, preferably screwed, to each other. This proximal end of the distal housing portion provides the space for arranging an additional component (holding means) without the need of a considerable adaptation of the rest of the injection mechanism.

Preferably, the injection device further comprises a guiding element which is connected in torque proof manner to the piston rod, is in removable torque proof engagement with the housing and guides the axial displacement of the piston rod during dispensing of an injection, wherein the holding means are arranged in the guiding member or between the guiding member and the housing.

When the holding means are arranged between the guiding member and the housing it is preferred that they are disposed adjacent to the guiding element on the distal end thereof.

The guiding element also has the function of a return element in order to screw the piston rod in distal direction by rotating the return element relative to the housing when the container of injection fluid is emptied and to be changed. In this case the proximal housing portion and distal housing portion are removed from each other. After exchanging the empty container against a new container, the two housing portions are mounted together. With reestablishing the torque proof engagement of the guiding element with the housing a new series of injections can start. The piston rod being arranged in its proximal end position can then be screwed back in his distal start position by rotating the guiding element relative to the housing with bringing the return element out of the torque proof engagement with the housing. Subsequently, in order to press on the piston of a newly inserted full container.

The dose setting means of the injection device comprise preferably a differential transmission for setting the dose, wherein the differential transmission comprises a plurality of threaded sleeves, wherein at least one sleeve has a thread pitch being different form the thread pitch of one another sleeve. This arrangement allows for example to have a rather great pitch of a dose setting member being operated directly by a patient, which leads to a rather big axial displacement recognized by the patient and allowing an easy display of the actually set dose and to have further sleeves having smaller pitches which transmit this rotational axial displacement to the threaded element on the piston rod, so that an according small dose can be set, wherein this dose needs a smaller axial displacement of the threaded element.

At last, it is preferred, that the dispensing of the injection dose is operated manually, where applicable with assistance through the pitch of the thread of a dose setting member.

BRIEF DESCRIPTION OF THE FIGURES

The invention is to be described exemplary and in no case restrictive with respect to the following figures.

FIG. 2 shows in a schematic perspective partial view the arrangement of holding means of a first embodiment in a guiding member.

FIGS. 3a and 3b show the guiding member and the holding means of the first embodiment before inserting the holding means (FIG. 3a) and after inserting the holding means (FIG. 3b).

FIG. 4 shows the holding means according to a second embodiment, namely in form of a disc on the piston rod.

FIG. 5 shows the holding disc in a schematic front view.

FIG. 6 shows in a schematic cross section according to the line VI-VI of FIG. 4 a possible elastic deformation of the holding means during axial displacement of the piston rod.

FIG. 7 shows in a schematic cross section different alternatives of holding means according to the first embodiment and to the second embodiment.

DETAILED DESCRIPTION

Figure 1:
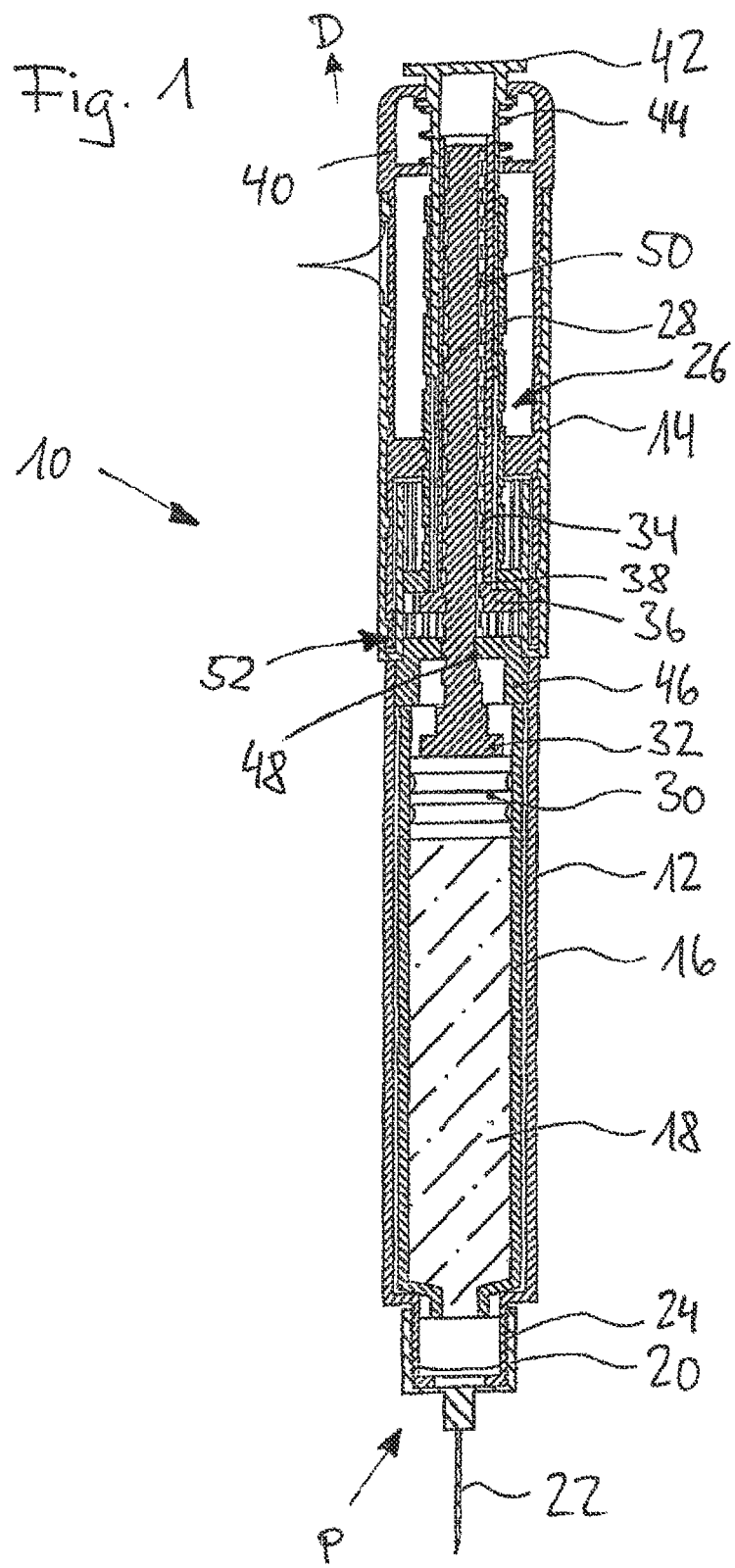
FIG. 1 is a longitudinal cross section of a known injection device of EP 1 610 848 B1, which shows the basic function of this device.

FIG. 1 is a longitudinal cross section of an injection device 10 having a proximal housing portion 12 and a distal housing portion 14. In the proximal housing portion 12 a container 16 filled with injection fluid 18 is received. On the proximal end P of housing portion 12 a cap 20 having integrated a needle 22 is screwed by means of a thread 24, so that a distal end of the needle 22 (not shown) is inserted into the container 16 in order to provide an outlet for injection fluid 18.

The distal housing portion 14 comprises a dose setting and injection mechanism 26, which is in detail described in EP 1 610 848 B1. The injection mechanism 26 comprises a piston rod 28 being axially displaceable with respect to the housing 12, 14 for dispensing injection fluid 18 from the container 16 by means of the piston 30, which is in contact with a proximal end 32 of the piston rod 28. The piston rod 28 has an outer thread 34 and is arranged torque proof with respect to the housing 12, 14, wherein torque proof means that the piston rod 28 is not rotatable in the assembled state of the injection device relative to the housing 12, 14.

Furthermore, the dose setting and injection mechanism 26 comprises a threaded element 36 having an inner thread 38 being in engagement with the outer thread 34 of the piston rod 28. This element 36 is designed such that its axial position relative to the housing 12 is changeable and the threaded element 36 is rotatable relative to the piston rod 28 and relative to the housing 12 during setting of an injection dose. This means, that during the setting of a dose the threaded element 36 is moved rotating on the piston rod 28 upon rotation of a dose setting member 40 axially in distal direction D. When a beforehand set dose is dispensed, the patient has to press a button 42 which is pre-stressed in a locked position by a spring 44, whereby the piston rod 28 is axially moved in a proximal direction due to the engagement with the threaded element 36 being beforehand moved a predetermined amount in distal direction D for setting a injection dose to be dispensed.

It has to be noticed, that the dose setting and injection mechanism 26 has further sleeves having different inner and outer threads with different or equal pitches, so that a rotational operation of the dose knob 40 leads to a differential transmission of this rotational axial movement to the threaded element 36. For more details, concerning this known dose setting and injection mechanism it is referred to EP 1 610 848 B1.

The piston rod 28 is held in torque proof manner by a guiding element 46 having a central opening 48 which is in mechanical cooperation, in particular engagement, with at least two planar oppositely disposed outer surfaces 50 cut in the outer thread 34 of the piston rod 28. In a preferred embodiment this guiding element 46 also serves as a return element in order to screw the piston rod 28 back in its distal start position according to FIG. 1 after removing an emptied cartridge 16 from the housing 12. For this purpose, the guiding and return element 46 is drawn out of housing portion 14 in order to screw piston 28 relative to the rest of the injection mechanism 26 by rotating element 46 relative to the housing portion 14.

In the following, two embodiments of holding means are explained with respect to FIGS. 2 to 7. These holding means are arranged close to a connection portion 52, where the proximal housing portion 12 and the distal housing portion 14 are removably attached, preferably screwed, to each other.

FIG. 2 shows in a schematic perspective partial view the piston rod 28 with its outer thread 34 and one of two opposed planar outer surfaces 50 for torque proof engagement with guiding element 46. Furthermore, the proximal end 32 of the piston rod 28 is apparent. The holding means 60 according to a first embodiment are inserted into the guiding element 46, as indicated in FIG. 2.

The holding means 60 of the first embodiment is a bent wire having substantially U-form as can be seen from FIG. 3a. The bent wire is preferably made of spring steel and the two branches-off the "U" are bent in such a manner, that clamping portions 62, 62' are formed having a convex shape with respect to the piston rod 28 inserted into the guiding element 46. The holding means or holding clamp 60 is inserted through a slit 46 in the guiding element 46 and is held axially fixed within the guiding element 46 but preferably with some play for enabling movement in a radial plane with respect to the axis of the piston rod 28.

When inserted in the guiding element 46, the clamping portions 62, 62' of the holding means 60 protrude with their respective convex wire portions in an opening 66 in which the piston rod 28 is axially guided and held in torque proof manner due to mechanical cooperation, in particular engagement, of the outer planar surfaces 50 of the piston rod 28 with corresponding planar surfaces 68 of the opening 66. This is best viewed in FIG. 3b being a front view from the proximal end according to arrow III of FIG. 3a.

Thus, the holding means 16 is automatically centered on the piston rod 28.

According to a second embodiment illustrated in FIGS. 4 to 6 the holding means 160 has the form a disc, wherein an inner contour 170 defines an opening through which the piston rod 28 passes. The holding means 160 is made of a plastic disc, and the contour 170 also defines two clamping portions 162, 162', which are in contact with the two planar surfaces 50 of the piston rod 28.

Such a holding disc 160 is arranged preferably adjacent to the guiding element 46 on the distal side thereof, as indicated by reference 52 in FIG. 1. During dispensing of an injection dose the holding disc 160 abuts against the guiding element 46 or against another fixed part of the housing and is therefore axially fixed with respect to the housing portion 14, so that it can act as holding means for the piston rod 28.

FIG. 6 shows simplified cross sections according to the line VI-VI of FIG. 4. In the right cross section of FIG. 6 the clamping portions 162, 162' are in a holding position. In this position the respective front faces 172, 172' are in full contact with the respective planar outer surface 50 of the piston rod 28. When the piston rod 28 is moved relative to the axially fixed clamping disc 160 in proximal direction M for dispensing a beforehand set injection dose, the preferably elastic clamping portions 162, 162' are slightly deflected, so that they are only in contact with a small area, namely an edge area 174, 174' of the front faces, 172, 172'. With such a configuration, the static friction in the holding position according to the right side of FIG. 6, is rather high, wherein the naturally smaller kinetic friction when the piston rod 28 moves with respect to the clamping disc 162 is further minimized by the deflection of the clamping portions 162, 162' due to the reduced contact area between the front faces 172, 172' and the respective outer surface 50 of the piston rod 28.

It has to be mentioned that in the schematic drawing of FIG. 6 the amount of elastic deformation during movement of the piston rod is exaggerated, so after ending of a movement of the piston rod 28 in the direction of arrow M the clamping portions 162, 162' are urged towards the holding position according to FIG. 6 (right hand side) without any effect on the position of the piston rod 28. Accordingly, there is no refraction of the piston rod in distal direction (opposed to arrow M of FIG. 6) due to the back-movement of the clamping portions 162, 162' in the rest position (right hand side). The clamping portions 162, 162' are urged by elastic restoring force towards the holding position.

FIG. 7 shows in a schematic and simplified manner possible alternatives of the cross section of the bent wire 60 according to the first embodiment, and of the clamp portions 162, 162' of the disc shaped holding means 160. As can be seen, the first cross section on the left is from a bent metal wire having a circle cross section. Alternatively, this cross section could be a circle segment in order to increase the contact area between the metal wire and the planar surface 50 of the piston rod 28. Furthermore, on the right side there is an alternative to the already proposed clamping portion 162, wherein the alternative clamping portion 162a has a front face 172a being in contact with the surface 50 of the piston 28 by two rips 176. Such an arrangement can also be advantageous in case of a resilient small deformation of the clamping portion 162, during movement of the piston rod 28 as indicated in FIG. 6 on the left side.

The holding means 60, 160 in form of a bent wire of spring steel or a disc of plastics allow to hold the piston rod 28 due to static friction between the clamping portions 62 and 62', 162, 162' and the planar surfaces 50 of the piston rod 28. This static friction is as high as to prevent any movement of the piston rod 28 due to inner friction of the injection mechanism 26 (FIG. 1) and/or due to plays within the injection mechanism 26 or the injection device 10 as whole. The symmetrical form of the holding means 60, 160 with respect to the longitudinal axis of the piston rod 28 leads to a steady clamping action on the piston rod 28. The forces exerted from each of the opposing clamping portions 62, 62' and 162, 162' neutralize each other in such a manner, that the clamping action does not evoke unilateral forces to be supported in radial direction by the housing such leading to a self-centering effect avoiding radial stresses acting between the piston rod and other parts of the injection device.

The invention claimed is:

1. Injection device, comprising
   a housing being adapted to receive in its proximal housing portion a container with an injection fluid and to receive in its distal housing portion a dose setting and injection mechanism, wherein the mechanism includes
   a piston rod being axially displaceable with respect to the housing for dispensing injection fluid from the container, wherein the piston rod has an outer thread and is arranged torque proof with respect to the housing,
   a dose setting means comprising a threaded element, which threaded element has an inner thread being in engagement with the outer thread of the piston rod, is designed so that its axial position relative to the housing is changeable, and is rotatable relative to the piston rod and relative to the housing during setting of an injection dose,
   wherein the threaded element is held in torque proof manner relative to the piston rod and to the housing during the injection of the beforehand set injection dose, wherein the threaded element and the piston rod are axially displaceable together with respect to the housing,
   wherein the mechanism further comprises a holding clamp being in contact with the piston rod to immobilize the axial displacement of the piston rod during use of the device except for the dispensing of the injection dose,
   wherein the holding clamp is axially fixed with respect to the housing and wherein the piston rod has two longitudinal planar outer surfaces cut in the outer thread and being arranged in parallel to each other on opposing sides of the piston rod, characterized in that the holding clamp is in contact with both parallel outer planar surfaces of the piston rod and exerts a compressive force on the piston rod wherein the holding clamp has two clamping portions each of which being in contact with a respective planar outer surface of the piston rod to frictionally engage with the piston rod and wherein the holding clamp is made from a bent metal wire and the clamping portions have a curvature being convex in direction to the piston rod and wherein the clamping portions of the holding clamp protrude with their respective convex wire portions in an opening of a guiding element in which the piston rod is axially guided and is held in torque proof manner due to an engagement of the outer planar surfaces of the piston rod with corresponding planar surfaces of the opening of the guiding element.

2. Injection device according to claim 1, characterized in that the holding means at least partially encompass the piston rod.

3. Injection device according to claim 1, characterized in that the two clamping portions are designed in such a manner, that they exert static friction on the piston rod being as high as to prevent unintentional axial displacement of the piston rod.

4. Injection device according to claim 3, characterized in that the two clamping portions are designed in such a manner, that they exert kinetic friction on the piston rod being as small as not to or only slightly interfere with the required axial displacement of the piston rod during dispensing an injection dose.

5. Injection device according to claim 1, characterized in that the clamping portions are elastically deformable.

6. Injection device according to any of claim 1, characterized in that the holding clamp is made from spring steel.

7. Injection device according to claim 1, characterized in that the holding clamp is arranged at a proximal end of the distal housing portion close to a connection portion where the proximal housing portion and the distal housing portion are removably attached to each other, preferably screwed to each other.

8. Injection device according to claim 7, characterized in that it further comprises a guiding element which is connected in torque proof manner to the piston rod, is in removable torque proof engagement with the housing and guides the axial displacement of the piston rod during dispensing of an injection, wherein the holding clamp is arranged in the guiding member or between the guiding member and the housing.

9. Injection device according to claim 8, characterized in that the holding clamp, when arranged between the guiding member and the housing, is disposed adjacent to the guiding element on the distal end thereof.

10. Injection device according to claim 1, characterized in that the dose setting means comprise a differential transmission for setting the dose.

11. Injection device according to claim 10, characterized in that the differential transmission comprises a plurality of threaded sleeves, wherein at least one sleeve has a thread pitch being different from the thread pitch of another sleeve.

12. Injection device according to claim 1, characterized in that the dispensing of the injection dose is operated manually.

* * * * *